United States Patent [19]

Homan et al.

[11] 4,145,359

[45] Mar. 20, 1979

[54] SHORT CHAIN LINEAR AMIDOSILOXANES

[75] Inventors: Gary R. Homan, Midland, Mich.; Louis H. Toporcer, Twinsburg, Ohio

[73] Assignee: Dow Corning Corporation, Midland, Mich.

[21] Appl. No.: 904,177

[22] Filed: May 8, 1978

[51] Int. Cl.$^2$ .............................................. C07F 7/10
[52] U.S. Cl. .......................... 260/448.2 N; 260/37 SB
[58] Field of Search ................................. 260/448.2 N

[56] References Cited

U.S. PATENT DOCUMENTS

| | | | |
|---|---|---|---|
| 3,488,371 | 1/1970 | Klebe | 260/448.2 N |
| 3,597,457 | 8/1971 | Robinson et al. | 260/448.2 N X |
| 3,776,933 | 12/1973 | Toporcer et al. | 260/448.2 E |
| 3,776,934 | 12/1973 | Toporcer et al. | 260/448.2 N |
| 4,008,198 | 12/1977 | Krohberger et al. | 260/37 SB |
| 4,020,044 | 4/1977 | Crossan et al. | 260/46.54 A |

Primary Examiner—Paul F. Shaver
Attorney, Agent, or Firm—Roger H. Borrousch; Edward C. Elliott

[57] ABSTRACT

Short chain linear amidosiloxanes of the formula

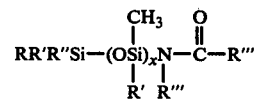

where R is a methyl, ethyl, or phenyl radical, R' is a methyl, ethyl, or 2-(perfluoroalkyl)ethyl radical, R" is a methyl or vinyl radical, and R'" is a methyl or ethyl radical and x is an integer of from 3 to 20 and mixtures of these amidosiloxanes are useful as treating agents for reinforcing silica fillers.

10 Claims, No Drawings

SHORT CHAIN LINEAR AMIDOSILOXANES

BACKGROUND OF THE INVENTION

1. Field of the Invention

This invention relates to amidosiloxanes and their mixtures.

2. Description of the Prior Art

Klebe in U.S. Pat. No. 3,488,371 describes linear difunctional silylamides of the formula

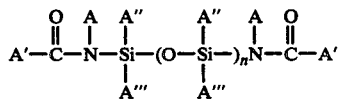

wherein A is alkyl or aryl when n is 0 or 1 and is in addition hydrogen when n is greater than 1 and A', A", and A''' are hydrogen, alkyl groups or aryl groups, and in addition A" and A''' are halogenated hydrocarbon groups and cyanoalkyl groups, and n is an integer of 0 to 1000 or more. Klebe describes that the amidosilyl compounds of his invention can be hydrolyzed with water in a solvent to yield rubbery siloxanes.

Toporcer and Crossan in U.S. Pat. No. 3,776,933 describe silanes of the formula

where D is methyl, ethyl, propyl, or phenyl, D' is methyl, ethyl, or phenyl, D" is a hydrocarbon radical, and x is 1, 2, or 3. These silanes are useful as crosslinking agents in silicone rubber, as hydrolysable silanes to make silicone resins, as chain extenders in silicone rubbers, as endblockers for silicone fluids, and as silylating agents.

Crossan and Toporcer in U.S. Pat. No. 4,020,044 describe a method of mixing hydroxyl endblocked polydiorganosiloxane and a silane of the formula

where R* is alkyl of one to four carbon atoms or phenyl and allowing the mixture to react to provide a polydiorganosiloxane of increased molecular weight which contains methylvinylsiloxane units which can be further reacted to give new polymers or cured products.

Krohberger in U.S. Pat. No. 4,008,198 claims a composition convertable to highly transparent elastomers comprising among other ingredients a nitrogen containing compound having at least one triorganosilyl group in which at least one nitrogen atom is linked directly to a silicon atom or via an oxygen atom, but no more than one triorganosilyl group is linked to a nitrogen atom and no more than one condensable group is linked to a silicon group. Among suitable compounds are aminoorganosiloxanes such as those corresponding to the $R_3^*Si(oSiR_2)_pNR_2^1$ wherein R* represents monovalent hydrocarbon radicals, halogenated aliphatic hydrocarbon radicals, and cyanoalkyl radicals, $R^1$ is hydrogen or a monovalent hydrocarbon radical having from 1 to 10 carbon atoms and p is a whole number having a value of from 1 to 20.

SUMMARY OF THE INVENTION

It is an object of this invention to provide an amidosiloxane or a mixture of amidosiloxanes consisting essentially of specific short chain linear amidosiloxanes suitable for use as treating agents for reinforcing silica fillers which can be used to make silicone elastomers.

Description of the Invention

This invention relates to an amidosiloxane of the formula

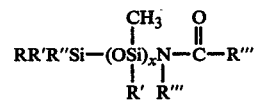

where R is a methyl, ethyl, or phenyl radical; R' is a methyl, ethyl, or 2-(perfluoroalkyl)ethyl radical in which the perfluoroalkyl radical contains 1 to 4 carbon atoms inclusive; R" is a methyl or vinyl radical; R''' is a methyl or ethyl radical; and x is an integer of from 3 to 20.

Amidosiloxanes of this invention can be prepared by reacting a short chain monochlorosiloxane with an amide in the presence of triethylamine as an acid acceptor and in the presence of an anhydrous inert solvent. A molar excess of the amide as compared to the monochlorosiloxane is used to assure that the reaction will go to completion. An excess of triethylamine is used to assure that all the halogen liberated by the reaction can be carried out by slowly adding either the monochlorosiloxane, the carbamide, or the triethylamine to a mixture of the two remaining ingredients. The reaction is rapid and exothermic, therefore it is preferred to add the selected ingredient to the mixture of the two remaining ingredients at a rate sufficiently slow to allow the proper control of the temperature through the use of external cooling means. The temperature should be controlled below 50° C. The amount of anhydrous inert solvent used should be enough to keep the reaction mixture fluid throughout the reaction. The insoluble triethylamine-hydrogen chloride salt formed by the reaction tends to thickened the reaction mixture. Stirring the mixture for a short period after the end of the addition, for instance one hour, assures completion of the reaction.

The triethylamine-hydrogen chloride salt can be removed from the reaction mixture by filtration. Means of excluding moisture from the reaction mixture during processing must be used because amidosiloxanes of this invention are sensitive to moisture and must be made and stored under essentially anhydrous conditions.

After removal of the triethylamine-hydrogen chloride salt, the filtrate can be used as a treating agent for reinforcing silica which can be used as a filler in silicone rubber. The filtrate can be further processed by a simple distillation to remove the solvent and unreacted ingredients. A device such as a Vigreaux column can be used to fractionate the reaction products to obtain particular molecular species.

The amidosiloxanes of this invention can also be prepared by reacting a short chain monochlorosiloxane with the metal salt of an amide in an inert organic solvent in a manner similar to the method disclosed by Toporcer and Crossan in U.S. Pat. No. 3,776,933 for preparing amidosilanes. Hurwitz and DeBenneville in U.S. Pat. No. 2,876,234 also describes a method for preparing amidosilanes.

The preferred method of producing the amidosiloxanes of this invention is the addition of triethylamine to a mixture of monochlorosilane and amide as described above.

A number of methods are known in the art for the preparation of the monochlorosiloxanes used in the preparation of the amidosiloxanes of this invention. One method is described by Brown and Hyde in U.S. Pat. No. 3,162,662 wherein a monochlorosilane can be reacted with hexaorganocyclotrisiloxane in the presence of acetonitrile and N,N-dimethylacetamide. For this invention the monochlorosilane would be RR′R″SiCl wherein R, R′ and R″ are defined above. The preferred monochlorosilanes would be trimethylchlorosilane and dimethylvinylchlorosilane. For this invention the hexaorganocyclotrisiloxane would be (MeR′SiO)$_3$ where Me is methyl and R′ is as defined above. The preferred cyclotrisiloxane would be hexamethylcyclotrisiloxane. This method provides a monochlorosiloxane which can then be used in the preparation of the amidosiloxanes of this invention. The monochlorosiloxanes having various x values can be prepared by allowing the reaction between the monochlorosilane and cyclotrisiloxane to continue over various periods of time and then separating the resulting mixture by using the spinning band distillation technique. The separations can be used to obtain single species or mixtures having the desired x value. A preferred value of x is from 3 to 6 with the most preferred value of 3. U.S. Pat. No. 3,162,662 is hereby incorporated by reference to show the monochlorosiloxanes and their preparation.

The amides used in the preparation of the amidosiloxanes of the present invention are well known in the art and are commercially available materials. The preferred amide is N-methyl acetamide.

The amidosiloxanes of this invention are species of short chain, linear amidosiloxanes. The amido radical attached to silicon on one end of the molecule is a readily hydrolysable group. The other end of the molecule can contain a vinyl group which allows further reaction of the amidosiloxane in any reaction that takes place with an unsaturated radical.

The novelty of the amidosiloxanes of the instant invention lies in the single hydrolysable amido radical in the molecule and the number of siloxane units per molecule. Such a construction is particularly effective when the triorganosiloxy radical is a vinyldiorganosiloxy. Such vinyl containing amidosiloxanes are particularly effective in further reactions, such as those in which the vinyl radical reacts with a hydrogen atom attached to a silicon atom, a reaction commonly used in crosslinking silicone elastomers.

The amidosiloxanes of this invention are useful for making monofunctional siloxanols by hydrolyzing the amido group. They may be used to add a short chain polydiorganosiloxane chain to any groups reacting with an amido group. They are particularly useful as treating agents for reinforcing silica which can be used in silicone rubber elastomers. Reinforcing silica treated with the amidosiloxanes of this invention is disclosed in application Ser. No. 904,048 filed on May 8, 1978, entitled "Treatment of Reinforcing Silicas With Amidosiloxanes," by Gary R. Homan, Myron T. Maxson, and Louis H. Toporcer and assigned to the same assignee as the present application.

The following examples are presented for illustrative purposes only and should not be construed as limiting the present invention which is properly delineated in the claims. In the examples, the methyl and vinyl radicals are represented by Me and Vi respectively.

Example 1

Into a 5 liter flask equipped with stirrer, condenser, drying tube, and additional funnel, there was placed 1,987 grams of a 50/50 by weight mixture of toluene and a monochlorosiloxane of the formula

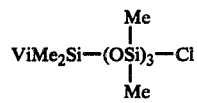

(993.5 grams, about 2.9 moles of the monochlorosiloxane), and then 330 grams (about 3.3 moles) of anhydrous triethylamine was added. To the resulting mixture there was added 240 grams (about 3.3 moles) of N-methylacetamide over a period of 30 minutes. An exothermic reaction was evident and external cooling with an ice-water bath was necessary. The salt formed by the reaction thickened the reaction mixture so that an additional two liters of anhydrous toluene was added. The reaction mixture was stirred for an additional hour after the complete addition of the N-methylacetamide. The salt was removed from the reaction mixture by vacuum filtration and the clear colored filtrate was strip distilled. The residue of the strip was 219 grams of

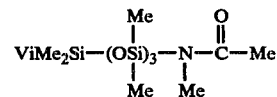

which had a boiling point of 87° C. at 130 Pa. The structure of this compound was confirmed by nuclear magnetic resonance, mass spectrometry, and infrared spectrometry.

Example 2

Into a 5 liter, 3-necked flask there was added 2000g (about 9 moles) of hexamethylcyclotrisiloxane and 627 g of dried acetonitrile. This mixture was gently heated to a temperature in the range of 50°–55° C. to dissolve all the siloxane in the acetonitrile. To this solution 62.7 g of N,N-dimethylacetamide was added with stirring. Then 1140 g (about 10.5 moles) of trimethylchlorosilane was added rapidly with stirring. The reaction was followed by testing small samples with the aid of a gas-liquid chromatography apparatus. The reaction was allowed to continue for 4 hours at 60° C.

The excess trimethylchlorosilane, unreacted hexamethylcyclotrisiloxane and acetonitrile were then stripped off. The residue of the strip was distilled using a Claisen head and vacuum to yield a product having a boiling point of approximately 55° C. at 104 Pa. The product was a monochlorosiloxane which contained 70% identified as

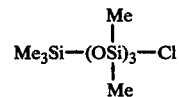

by nuclear magnetic resonance spectrometry.

A 3 liter, 3-necked flask was equipped with stirrer, thermometer, and addition funnel. To the flask there was added 515 g of the monochlorosiloxane produced above (about 1.09 moles), 87.6 g (about 1.2 moles) of N-methylacetamide and 1.5 liters of dry toluene, and then 127.2 g (about 1.2 moles) of triethylamine was slowly added through the addition funnel. The reaction mixture exothermed to 42° C., and then it was allowed to react for two additional hours.

The amine salt formed during the reaction was removed by filtration without allowing the reacted mixture to contact moisture. The filtrate was stripped of solvent under vacuum and the residue was fractionated with a Vigreaux column under vacuum. The product fractions boiling at 102° C. at 260 Pa. were combined to give a 90–95% yield of product of the formula

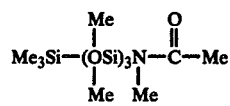

Example 3

A 3-necked flask was equipped with stirrer, thermometer, and addition funnel. To the flask there was added 666 g (3 moles) of hexamethylcyclotrisiloxane and 209 g of dried acetonitrile. This mixture was heated gently to 50°–55° C., then 20.9 g of N,N-dimethylacetamide was added, and then 422 g (3.5 moles) of dimethylvinylchlorosilane was rapidly added with stirring. The reaction mixture was stirred overnight. After 20 hours the unreacted hexamethylcyclotrisiloxane, excess dimethylvinylchlorosilane and acetonitrile were stripped off at room temperature under vacuum. The remaining material was distilled through a Vigreaux column.

The distillation fractions numbered one through four were combined to give 316 g of product containing 97 percent monochlorosiloxane of the formula

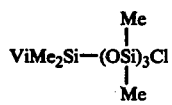

The fifth fraction, approximately 50 g of product, contained 80% monochlorosiloxane of the same formula.

A 3 liter, 3-necked flask was equipped with stirrer, thermometer, and addition funnel. To the flask was added 316 g (0.92 mole) of

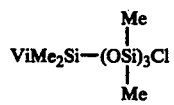

76.7 g (about 1.05 moles) of N-methylacetamide, and 1.5 liters of dry toluene, and then 106 g (about 1.05 moles) of triethylamine was added drop wise through the addition funnel. The reaction mixture exothermed to 33° C., was stirred for 1 hour and then the amine salt was removed by filtration without allowing the reacted mixture to contact moisture. The toluene was stripped off under vacuum and the residue was fractionated on a Vigreaux column under vacuum. The fractionated product had a boiling point of 78°–79° C. at 13 Pa, and was identified as

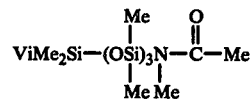

by nuclear magnetic resonance techniques.

That which is claimed is:

1. An amidosiloxane of the formula

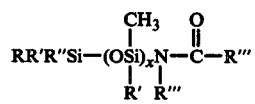

where R is a methyl, ethyl, or phenyl radical; R' is a methyl, ethyl, or 2-(perfluoroalkyl) ethyl radical in which the prefluoroalkyl radical contains 1 to 4 carbon atoms inclusive; R" is a methyl or vinyl radical; R''' is a methyl or ethyl radical; and x is an integer of from 3 to 20.

2. The amidosiloxane of claim 1 where R and R' are methyl radicals and R" is a vinyl radical.

3. The amidosiloxane of claim 2 where x is an integer of from 3 to 6.

4. The amidosiloxane of claim 2 where x is 3.

5. The amidosiloxane of claim 1 where R, R', and R" are methyl radicals.

6. The amidosiloxane of claim 5 where x is an integer of from 3 to 6.

7. The amidosiloxane of claim 6 where x is 3.

8. A composition consisting essentially of a mixture of amidosiloxanes of claim 1 in which x is an integer of from 3 to 20 and has an average value of from greater than 3 to less than 20.

9. A composition consisting essentially of a mixture of amidosiloxanes of claim 2 in which x has an average value of from greater than 3 to 6.

10. A composition consisting essentially of a mixture of amidosiloxanes of claim 5 where x has an average value of from greater than 3 to 6.

* * * * *

UNITED STATES PATENT AND TRADEMARK OFFICE
CERTIFICATE OF CORRECTION

PATENT NO. : 4,145,359
DATED : March 20, 1979
INVENTOR(S) : Gary R. Homan; Louis H. Toporcer It is certified that error appears in the above-identified patent and that said Letters Patent are hereby corrected as shown below:

Column 1, line 59; the formula reading $R_3^*Si(oSiR_2)_pNR_2^1$ should read $R_3^*Si(OSiR_2)_pNR_2^1$ Column 2, lines 9-12; the formula reading 
$$RR'R''Si-(O\overset{CH_3}{\underset{R'}{Si}})_x\overset{}{\underset{R'''}{N}}-\overset{O}{\overset{\|}{C}}-R'''$$

should read 
$$RR'R''Si-(O\overset{CH_3}{\underset{R'}{Si}})_x-\overset{}{\underset{R'''}{N}}-\overset{O}{\overset{\|}{C}}-R'''$$

Signed and Sealed this

Twenty-fifth Day of August 1981

[SEAL]

Attest:

GERALD J. MOSSINGHOFF

Attesting Officer    Commissioner of Patents and Trademarks